United States Patent
Mastrorio et al.

(10) Patent No.: US 6,325,830 B1
(45) Date of Patent: Dec. 4, 2001

(54) CEMENT RESTRICTOR

(75) Inventors: Brooke W. Mastrorio, Lakeville; Pierre S. Ostiguy, Rochester, both of MA (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/148,649

(22) Filed: Sep. 4, 1998

Related U.S. Application Data

(60) Division of application No. 08/852,004, filed on May 6, 1997, now Pat. No. 5,997,580, which is a continuation-in-part of application No. 08/828,035, filed on Mar. 27, 1997, now Pat. No. 5,879,403.

(51) Int. Cl.$^7$ .................................................. A61F 2/28
(52) U.S. Cl. .......................................... 623/23.48; 606/95
(58) Field of Search ........................... 623/16.11, 23.48; 606/62, 63, 76, 92, 95, 99, 198, 200

(56) References Cited

U.S. PATENT DOCUMENTS

| | | | |
|---|---|---|---|
| 4,245,359 | 1/1981 | Stuhmer | 3/1.9 |
| 4,262,665 * | 4/1981 | Roalstad et al. | |
| 4,276,659 | 7/1981 | Hardinge | 3/1.9 |
| 4,302,855 | 12/1981 | Swanson | 3/1.9 |
| 4,344,190 | 8/1982 | Lee et al. | 3/1.9 |
| 4,447,915 | 5/1984 | Weber | 3/1.9 |
| 4,462,394 | 7/1984 | Jacobs | 128/92 C |
| 4,559,936 | 12/1985 | Hill | 128/92 R |
| 4,657,549 * | 4/1987 | Keller | 623/16 |
| 4,686,973 | 8/1987 | Frisch | 128/92 YZ |
| 4,697,584 | 10/1987 | Haynes | 128/92 VQ |
| 4,745,914 | 5/1988 | Frey et al. | 128/92 VP |
| 5,078,746 * | 1/1992 | Garner | 623/23.48 |
| 5,092,891 | 3/1992 | Kummer et al. | 623/16 |
| 5,340,362 | 8/1994 | Carbone | 623/15 |
| 5,383,932 * | 1/1995 | Wilson | 623/23.48 |
| 5,443,478 * | 8/1995 | Purdy | 606/200 |
| 5,540,701 * | 7/1996 | Sharkey et al. | 606/153 |
| 5,549,694 | 8/1996 | Noiles et al. | 623/22 |
| 5,618,301 * | 4/1997 | Hauenstein et al. | 606/198 |
| 5,690,671 * | 11/1997 | McGurk et al. | 606/200 |
| 5,749,891 * | 5/1998 | Ken et al. | 606/200 |

OTHER PUBLICATIONS

Brochure entitled *Cemented Hip Systems Surgical Technique*, Johnson & Johnson Orthopaedics, pp. 1–9, dated 5/96.

Article entitled *Shape Memory Alloys*, by C.M. Wayman, pp. 49–56, reprinted from Materials Research Society MRS Bulletin, vol. 18 No. 4, Apr. 1993.

* cited by examiner

*Primary Examiner*—Michael J. Milano
(74) *Attorney, Agent, or Firm*—Nutter, McClennen & Fish, LLP

(57) ABSTRACT

A cement restrictor is provided for creating a fixed obstruction within a bone. An exemplary cement restrictor includes a member or body that is expandable or transitionable from a first diameter to a second diameter.

18 Claims, 8 Drawing Sheets

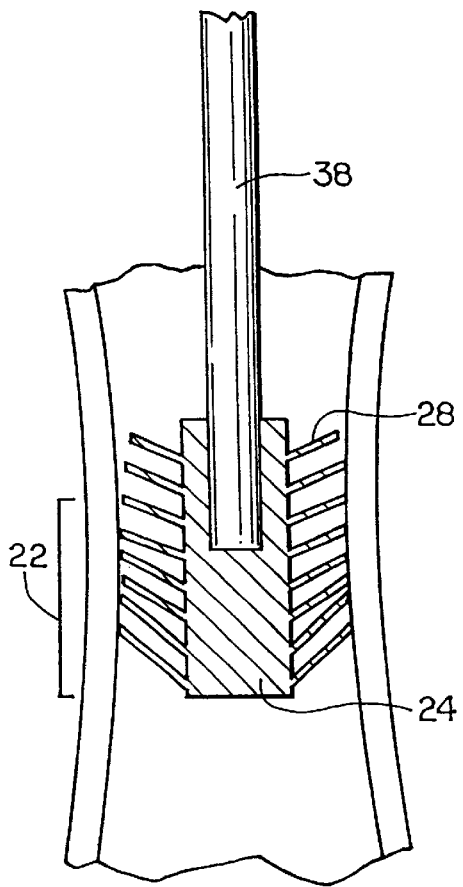
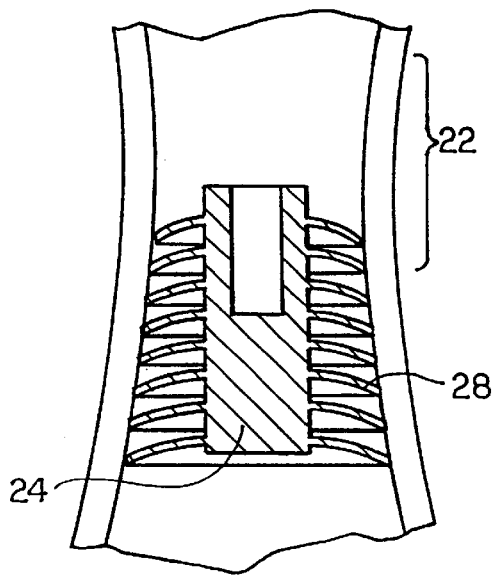
*FIG. 10*  *FIG. 11*

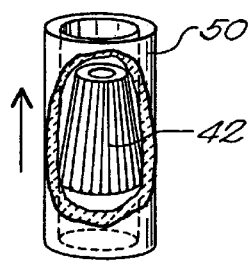
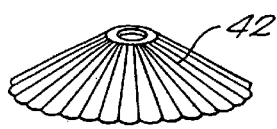
FIG. 24  FIG. 25
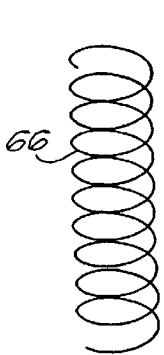 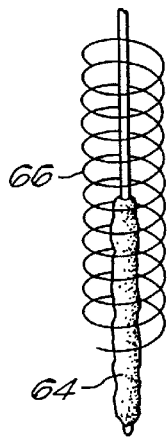 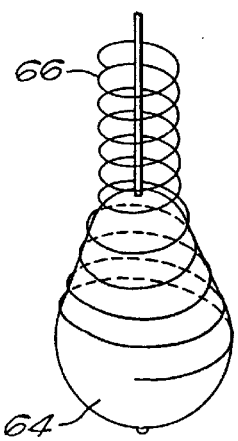 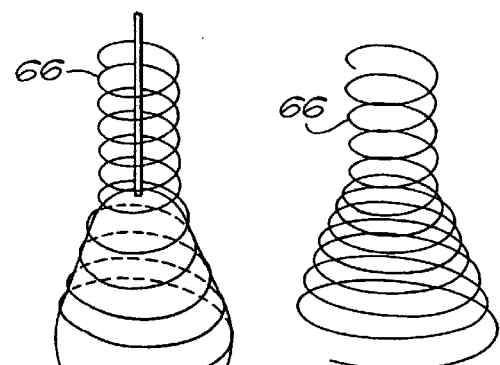
FIG. 26  FIG. 27  FIG. 28  FIG. 29
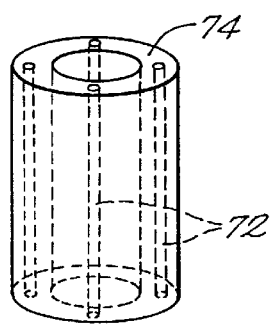 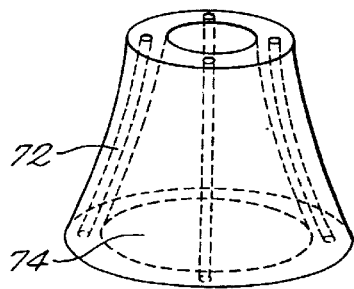
FIG. 30  FIG. 31

CEMENT RESTRICTOR

CROSS REFERENCE RELATED APPLICATIONS

This application is a division of U.S. patent application Ser. No. 08/852,004 filed May 6, 1997, entitled CEMENT RESTRICTOR now U.S. Pat. No. 5,997,580, which is a continuation-in-part of U.S. patent application Ser. No. 08/828,035 filed Mar. 27, 1997, entitled BISTABLE CEMENT RESTRICTOR now U.S. Pat No. 5,879,403.

STATEMENT REGARDING FEDERALLY-SPONSORED RESEARCH

Not Applicable.

FIELD OF THE INVENTION

The present invention relates to a device used in hip arthroplasty, and more particularly to a structure for creating a cement restriction or blockage within a bone.

BACKGROUND OF THE INVENTION

Arthroplasty procedures, such as a total hip replacement, can require the removal of the femoral head and neck, followed by implantation of an artificial hip stem into a reamed portion of the femoral medullary canal. Some hip arthroplasty procedures call for the use of bone cement to secure the hip stem within the medullary canal. For procedures that call for cement, it is generally undesirable to allow the cements to infiltrate the medullary canal to an uncontrolled depth and volume. Therefore, a hip arthroplasty procedure can include the step of placing an obstruction within the medullary canal in an attempt to restrict or block the flow of cement.

Not infrequently, the obstruction is merely a partially hardened or cured ball of cement placed into the canal and held in place by friction fit with the wall of the canal. This makeshift obstruction is easily dislodged by the distal end of the hip stem if the cement ball is not inserted deep enough into the canal. Additionally, the ball of cement is readily displaced when pressurized cement is added to the medullary canal to bind the stem in place. If the cement ball is fractured and/or if it falls beyond a narrow central region of the femur known as the isthmus, the pressurized cement does not properly infiltrate the bone and air pockets or pores are created in the cement. The imperfection laden hardened cement thus provides a poor interlock with the bone and stem and it is susceptible to cracking. Poor mechanical interlock and cement failure causes the stem to loosen. This undesirable occurrence often requires that the joint be replaced in a procedure known as a revision.

Revision surgery and/or procedures requiring a "long" hip stem are especially problematic with an application that calls for pressurized cement. Specifically, the distal end of a revision stem ultimately extends further into the medullary canal than an original "normal" stem because additional bone is cut-away during removal of the original stem in preparation to prepare for implantation of the revision stem, or poor quality bone stock forces a larger stem to be used to secure the stem more distally in the canal to reach better quality bone to achieve implant stability. Whereas the distal end of the original stem may extend to a point before or above the isthmus, and thus above the ball of cement, the distal end of the revision stem may extend beyond the isthmus.

Structures other than cement balls are also known for creating a blockage within a medullary canal. For example, FIG. 1 illustrates a known device 10 including a tapered body 12 having a first end 14, a second end 16, and fins 18 that extend radially from the body. Each fin 18 is resilient and can be flexed toward the first end 14 or the second end 16 of the body 12 as shown in the illustration by dashed lines. Although it is possible to maintain one or more fins 18 in a flexed condition by applying pressure to the fin(s) or placing them in a confined space to elastically deform them, once the pressure is relieved or the device is removed from confinement, the fin(s) will always return to their original position unless they have been plasticily deformed. Thus, the fins 18 and the device 10 can be described as only having a single stable state.

In use, a single stable state device 10 can be well suited to the tasks of creating a blockage within a reamed medullary canal 20 above an isthmus region 22 as shown in FIG. 2. It will be noted that the fins 18 are deformed different amounts depending on where they are within the tapered medullary canal 20. The body 12 and the fins 18 can have a thickness such that even when the fins are fully compressed against the body, the device 10 is broader than the isthmus 22 to prevent the device from being readily pushed beyond the isthmus. Thus, in a typical pressurized cement application, the pressurization of the cement does not dislodge the device.

By contrast with an above-the-isthmus application, the device 10 is totally unsited for beyond-the-isthmus applications as shown in FIG. 3. Specifically, once some of the fins 18 of the device 10 move beyond the isthmus, there is less and less mechanical interlock with the bone and even the application of low pressure causes the plug to be dislodged. Were the device 10 to be deliberately passed beyond the isthmus and then pulled back up into the narrow passage as shown in FIG. 4, the flexed fins 18 would urge the device down and away from the isthmus.

SUMMARY OF THE INVENTION

The present invention overcomes the disadvantages of known techniques and devices by providing a cement restrictor that is particularly well suited for revision arthroplasty. An appropriately dimensioned cement restrictor can create a fixed obstruction at any selected point within a long bone, particularly at points beyond the isthmus.

The cement restrictor includes a single or multiple finned body having a first stable state and a second stable state. In the first stable state, the cement restrictor is narrower than in the second stable state. While the cement restrictor is readily transitionable from the first stable state to the second stable state, the transition can be irreversible.

An illustrative embodiment of the cement restrictor includes a body having a first end and a second end. Bistable fins extend radially from the body and are irreversibly movable from a first stable state to a second stable state. The fins are concave with respect to the first end of the body in the first stable state and convex with respect to the first end of the body in the second stable state. The diameter of each fin is larger in the second stable state than in the first stable state.

Other embodiments of inventive cement restrictors are shown that include shape memory material that changes shape or dimension(s) in response to temperature and/or stress.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 10 shows an exemplary cement restrictor in accordance with the invention being inserted into a reamed bone portion, wherein the cement restrictor is in a first stable state;

FIG. 11 depicts the cement restrictor of FIG. 10 in an installed configuration beyond the isthmus, wherein the cement restrictor is in a second stable state;

FIG. 24 illustrates a sheath used to maintain a cement restrictor in a reduced diameter state;

FIG. 25 illustrates the cement restrictor of FIG. 24 in an increased diameter state;

FIG. 26 shows an internal structure of an embodiment of a cement restrictor in a first stable state;

FIG. 27 shows a balloon catheter in association with the cement restrictor of FIG. 26;

FIG. 28 depicts the balloon of FIG. 27 being inflated to transition the cement restrictor from a first stable state to a second stable state;

FIG. 29 depicts the cement restrictor in a stable, expanded state;

FIG. 30 illustrates another embodiment of a cement restrictor in a first stable state;

FIG. 31 illustrates the cement restrictor of FIG. 30 in a second expanded, configuration;

DETAILED DESCRIPTION OF THE INVENTION

Figure 1:
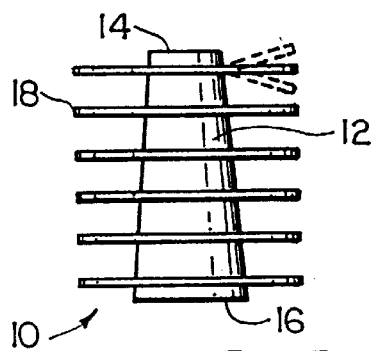
FIG. 1 is an elevational view of a prior art cement restrictor.
Figure 3:
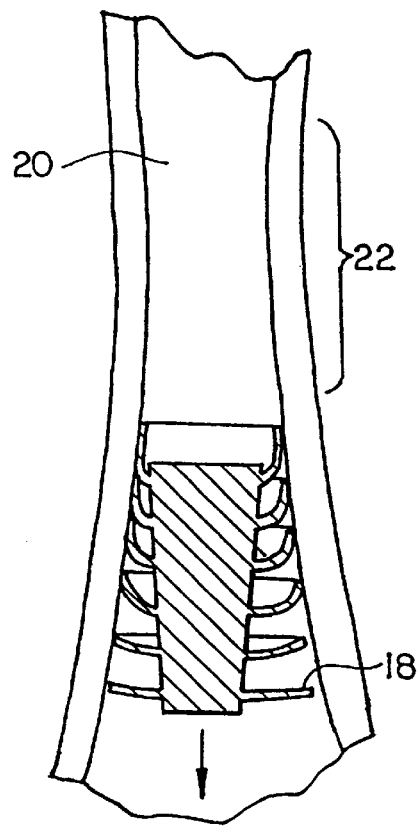
FIG. 3 is a sectional view of a reamed bone, wherein the prior art cement restrictor of FIG. 1 has been pushed beyond the isthmus of the bone.
Figure 2:
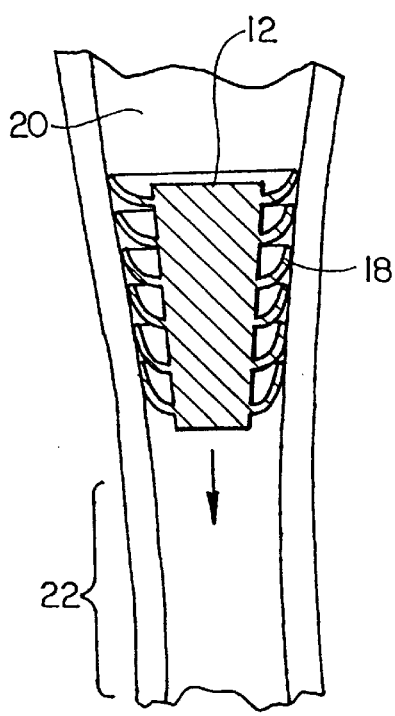
FIG. 2 is a sectional view of a reamed bone, wherein insertion of the prior art cement restrictor of FIG. 1 is depicted.
Figure 4:
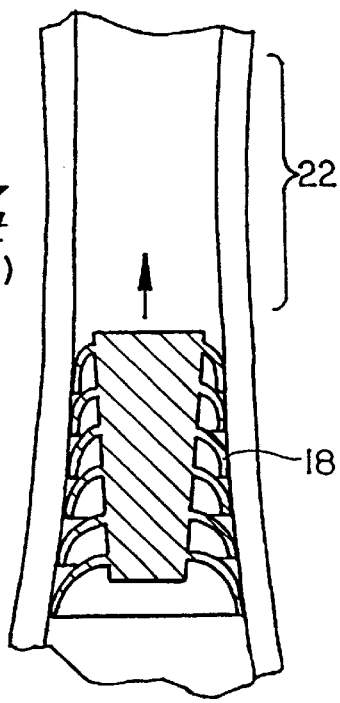
FIG. 4 is a sectional view of a reamed bone, wherein the prior art cement restrictor of FIG. 1 has been pushed completely beyond the isthmus and is being pulled back toward the isthmus.
Figure 5:
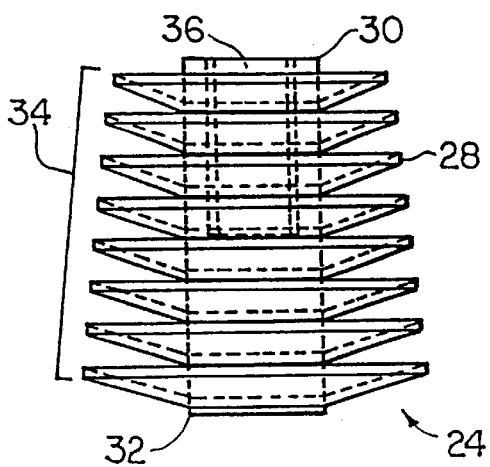
FIG. 5 is an elevational view of a cement restrictor in accordance with the present invention in a first stable state.
Figure 6:
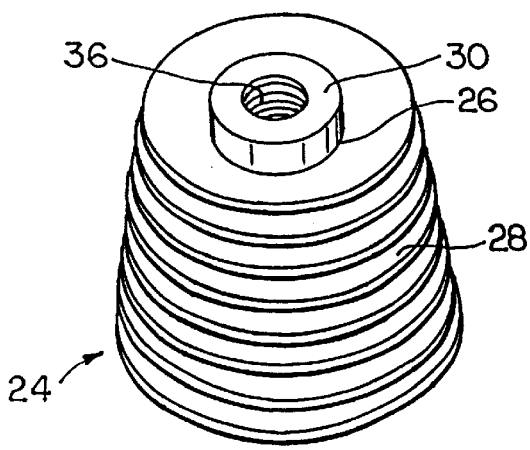
FIG. 6 is a perspective view of the cement restrictor of FIG. 5.

FIGS. 5 and 6 are side and perspective views, respectively, of a cement restrictor 24 in accordance with the invention that includes a body 26 from which one or more fins 28 extend radially in a first stable state. As used herein, "stable state" means a condition in which a structure(s) (e.g., the fins) retains a predetermined shape, configuration, or orientation with respect to another element(s) (e.g., the body); and even if the structure(s) is deformed within a selected range of deformation, the structure(s) will rebound or return to the predetermined shape or configuration in the absence of additional or externally applied energy or forces. For example, as described in greater detail below, it can be possible to deform the fins 28 by applying pressure to them in a first direction, and upon discontinuance of the pressure, the fins return to their pre-deformation orientation; whereas applying pressure to the fins in a second direction causes the fins to be deformed such that after the pressure has been discontinued, the fins do not return to their pre-deformation orientation.

Continuing to refer to FIGS. 5 and 6, an elongate body 26 has a first end 30, a second end 32, and an intermediate portion 34 between the first and second ends Although each fin 28 can be identically dimensioned, the exemplary fins 28 are of different diameters. For example, the fin 28 near the first end of the body has the smallest diameter and the fin nearest the second end has the greatest diameter. Each successive fin 28 from the first end of the body to the second end thereof is broader than the preceding fin. Thus, because the body 26 has a uniform diameter, the cement restrictor 24 has a tapered profile. The specific fin dimensions and the overall profile of the cement restrictor 24 are determined by the anticipated medullary wall contours at an intended site of obstruction. For an embodiment of the cement restrictor having fins 28 of different diameters, but having substantially uniform thickness, the broader fins are more flexible than the less broad fins to allow the fins to be deformed enough to fit through an opening of a selected size, such a reamed isthmus. However, the spacing of the fins 28 from each other inhibits the fins from being excessively deformed.

Figure 7:
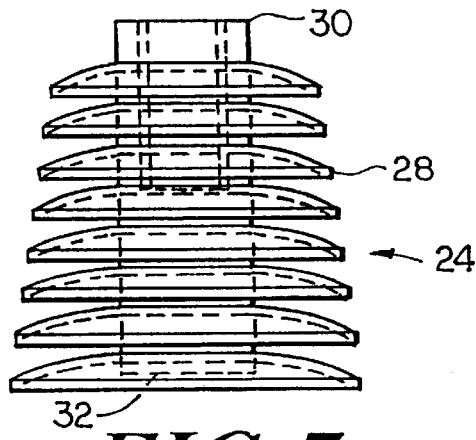
FIG. 7 is an elevational view of the cement restrictor of FIGS. 5 and 6, showing the cement restrictor in a second stable state.

It should be noted that while axial pressure applied to the body 26 in the direction of the second end of the body, or axial pressure applied to the fins in the direction of the first end of the body, or a combination thereof, can cause the fins 28 to be deformed, as shown in FIG. 10, the cement restrictor 24 remains in the first stable state. By contrast, axial pressure applied to the body in the direction of the first end of the body, or axial pressure applied to the fin in the direction of the second end of the body, or a combination thereof, can cause the fins to be deformed, as shown in FIG. 7, to transition the cement restrictor from the first stable state to the second stable state. The first stable state of the cement restrictor is notable for the fins 28 being angled toward the first end of the body or fins which are convex with respect to the second end of the body to facilitate insertion of the cement restrictor into a medullary canal. In its second stable state, shown in FIG. 7, the cement restrictor 24 is notable for the angulation of the fins toward the second end of the body or fins which are concave with respect to the second end of the body to inhibit movement of the cement restrictor with respect to the bone as shown in FIG. 11. The cement restrictor can be configured so as to be irreversible. In other words, it cannot be transitioned from the second stable state to the first stable state. However, even in the second stable state the fins can flex, yet return or urge to return a to the pre determined configuration or shape that defines the second stable state.

The embodiment of the cement restrictor shown in FIGS. 5–7 includes eight fins 28. Although the number of fins many be different for other embodiments, and can be as few as a single fin, it is desirable to have a large number of fins to maximize the surface for mechanical interlock between the fins and the bone, to ensure that the cement restrictor does not become displaced during subsequent cement pressurization.

In an exemplary embodiment, the fins 28 are made of a resilient material such as polyethylene and they are joined to or are integral with the body 26 so as to be bistable as described above. However, the fins 28 can also be made of a temperature responsive, stress responsive, or super elastic shape memory alloy (SMA) as described below. Thus, the fins 28 can be in the first stable state at a first temperature or stress condition and in the second stable state at a second temperature or stress condition. In an exemplary embodiment, the cement restrictor is chilled to below (or heated above) body temperature to place it in the first stable state, at which point the cement restrictor is readily insertable into a bone. As the fins warm (or cool) to a temperature in the normal range of body temperatures, the fins transition to the second stable state and engage the bone. Additionally, even though the fins are shown as discrete elements, other embodiments include a single, helical fin.

Continuing to refer to FIG. 5 and 6, the body 26 can include an engagement feature to allow it to be manipulated with surgical tools to position the cement restrictor and to transition it from the first stable state to the second stable state. As illustrated, the body 26 includes a recess or socket 36 into which a tool 38 (shown in FIG. 10) can be inserted to push the cement restrictor 24 through the medullary canal and with which axial pressure can be applied to the body. The socket 36 can include a resilient surface or sleeve to help temporarily hold the tool 38 in an engaged relationship with the cement restrictor 24. In another embodiment, the socket 36 and the tool 38 are threaded. The specific features of the tool and its engagement with the cement restrictor are not of particular importance with respect to the present invention.

Figure 8:
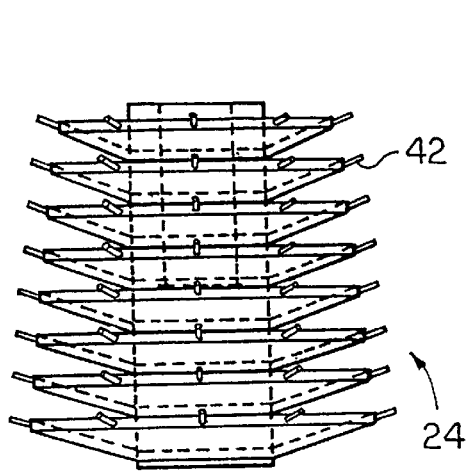
FIG. 8 is an elevational view of an alternative embodiment of a cement restrictor in accordance with the invention in a first stable state.
Figure 9:
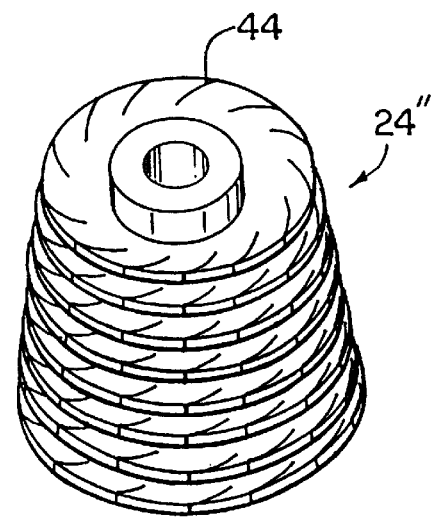
FIG. 9 is an elevational view of yet another embodiment of a cement restrictor in accordance with the invention in a first stable state.

Although fins 28 in the second stable state are capable of holding the cement restrictor 24 in place within a bone, other embodiments include fins with roughened peripheral regions, such as the edge of the fin and an adjacent surface portion. In yet other embodiments, such as shown in FIG. 8, barbs 42 can extend from the periphery of one or more fins of restrictor 24'. The cement restrictor can be twisted to cause the barbs to dig into the bone. FIG. 9 illustrates yet another embodiment of the cement restrictor 24" adapted to enhance interlock with a bone surface, wherein cuts 44 extend radially through one or more fins. When the cement restrictor is twisted, the fins separate at the cuts and the edges of the fins dig into the bone.

FIG. 10 illustrates the an exemplary cement restrictor 24 in accordance with the invention being pushed into a medullary canal with an insertion tool 38. The cement restrictor is in a first stable state and deformation of fins 28 at the isthmus region should be noted.

FIG. 11 shows the cement restrictor of FIG. 5 in place beyond the isthmus. The insertion tool 38 (or other tool) has applied a tractive axial force to the body to cause the fins to transition to a second stable state, and the cement restrictor is shown in the second stable state with the tool(s) removed. The fins engage the bone wall with sufficient force to permit pressurized cement to be added to the medullary canal in a manner known to those skilled in the art without dislodging the cement restrictor.

In addition to the embodiments illustrated above, other embodiments of cement restrictors are now described that benefit from the properties of shape memory materials, as well as traditional materials such as metal wire, to provide structures that can be expanded from a first diameter to a second diameter along a selected axis and/or which can be transitioned from a first stable configuration to a second stable state configuration. The capability of expansion permits a structure to be passed through an opening or passage, such as an isthmus of a medullary canal, in a reduced diameter state. Once past the opening or the passage (such as the isthmus), the structure is expanded to a diameter greater than that of the opening or passage. Depending upon the application, the structure can have many uses such as being a plug, a cement restrictor, or an anchor.

Figure 12:
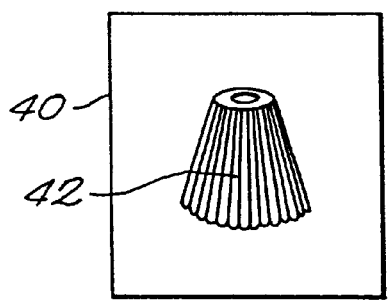
FIG. 12 depicts another embodiment of a cement restrictor in a first stable state.
Figure 13:
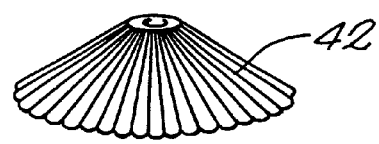
FIG. 13 illustrates the cement restrictor of FIG. 12 in a second stable state.
Figure 14:
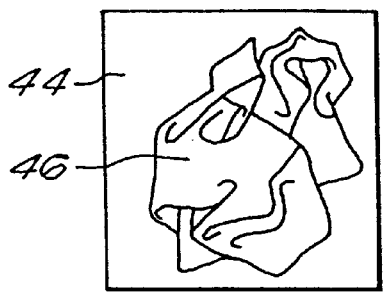
FIG. 14 depicts another embodiment of a cement restrictor in a first stable state.
Figure 15:
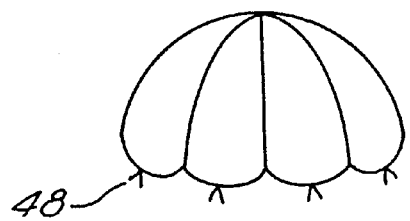
FIG. 15 illustrates the cement restrictor of FIG. 14 in a second stable state.

For example, FIG. 12 depicts a sheet of shape memory material 40, such as Nitinol, that has been rolled and/or folded (and trimmed as required) to provide a roughly conical structure 42 having a first diameter. When stress on the folded structure is released or reduced, the cement restrictor 42 expands. Although a shape memory material can be folded in a particular manner as shown with respect to FIG. 12, FIG. 14 depicts another embodiment wherein a sheet of shape memory material 44 is merely crumpled to provide a reduced diameter cement restrictor 46 and later allowed or caused to expand to provide a cement restrictor 48 having an increased diameter (FIG. 15). Prior to being crumpled, the memory material 44 can be cut or trimmed to cause the material to assume a particular configuration when it is fully expanded, as shown in FIG. 15. For example, the material 44 can be cut to provide barbs along the periphery of the cement restrictor.

FIG. 24 illustrates a sheath 50 for constraining a cement restrictor 42 in a stressed condition. When the sheath is separated from the cement restrictor 42, the cement restrictor expands as shown in FIG. 25. In an exemplary procedure, a sheath enclosed cement restrictor 42 is inserted into the medullary canal of a bone. The cement restrictor is held in position with a tool (not shown) at a desired obstruction site and the sheath is removed. The cement restrictor expands and forms a blockage in the bone. Although, the sleeve 50 is a cylindrical body, in other embodiments it is a band that surrounds only a portion of the cement restrictor 42.

Figure 16:
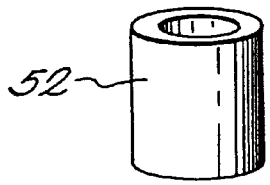
FIG. 16 depicts another embodiment of a cement restrictor in a first stable state.
Figure 17:
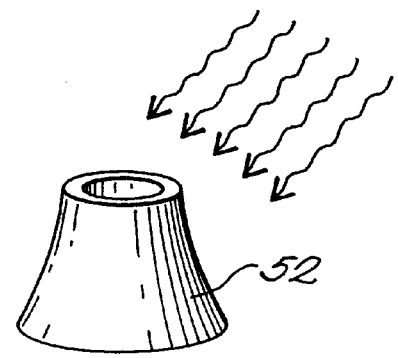
FIG. 17 illustrates the cement restrictor of FIG. 16 in a second stable state.
Figure 18:
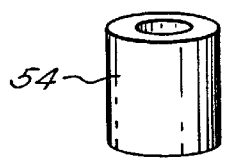
FIG. 18 depicts yet another embodiment of a cement restrictor in a first stable state.
Figure 19:
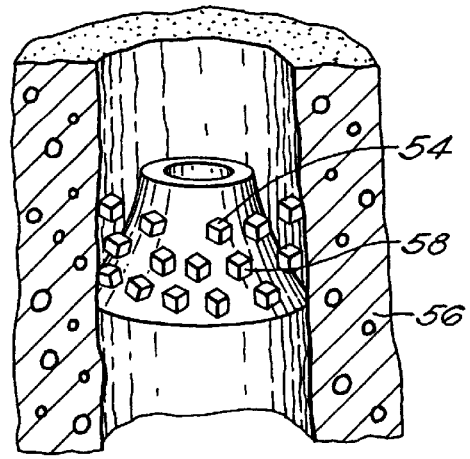
FIG. 19 shows the cement restrictor of FIG. 18 within a bone as the restrictor transitions to a second stable state.

Whereas FIGS. 12–15, 24 and 25 illustrate embodiments that are placed under stress, then released and allowed to expand, FIGS. 16–19 illustrate embodiments that change shape in response to a temperature change. For example, FIG. 16 illustrates a cylindrical structure 52 including a memory material. When heated as shown in FIG. 17, portions of the structure 52 expand in varying degrees to provide a tapered structure. FIG. 18 depicts a cylindrical structure 54 that transitions to an expanded stable state upon the application of cold. FIG. 19 shows the structure 54 within a bone 56, partially covered with crushed ice 58.

Figure 20:
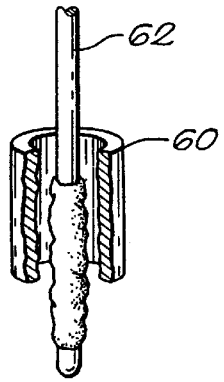
FIG. 20 depicts a cement restrictor partially cut away to reveal a balloon catheter.
Figure 21:
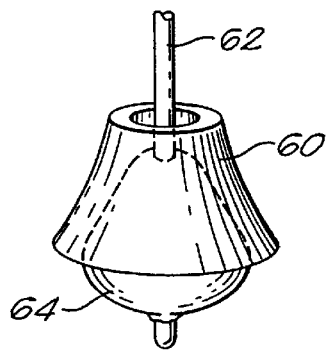
FIG. 21 depicts the balloon of FIG. 20 being inflated to transition the cement restrictor from a first stable state to a second stable state.

Yet other embodiments of the cement restrictor are stable in an unconstrained state, and are transitioned to a second stable state through the application of stress. For example, FIG. 20 depicts a cylindrical cement restrictor 60 partially cut away to reveal a portion of a balloon catheter 62 within a space defined by the cement restrictor. When a balloon portion 64 of the catheter 62 is inflated, it forces at least a portion of the cement restrictor outward as shown in FIG. 21. When the balloon is deflated, the cement restrictor 60 remains in the expanded configuration. For a temperature responsive memory material, the balloon could be filled with a heated or cooled fluid.

FIGS. 26–29 illustrate an internal structural element 66 for an embodiment of a cement restrictor such as that shown in FIGS. 20 and 21. The structural element 66 acts as a skeleton around and over which a boicompatible material is formed. Although the structural element 66 can be a memory material, it can also be a simple metal wire that is deformable. As illustrated in FIG. 27 the balloon catheter 62 is within a space defined by the cement restrictor. When a balloon portion 64 of the catheter 62 is inflated, it forces at least a portion of the cement restrictor 66 outward as shown in FIG. 28. When the balloon is deflated, the cement restrictor 60 remains in the expanded configuration as shown in FIG. 29.

In still another embodiment, the structure 66 is not initially covered with a biocompatible material and it alone is placed into the bone and expanded as shown in FIG. 28. While the balloon is inflated, bone cement is poured onto the structure 66 and allowed to harden. The balloon is subsequently deflated and a cement restrictor, including bone cement with a wire reinforcement, remains in place within the bone. A simple plug or cover (not shown) can be placed in or over any remaining opening defined by the cement restrictor in this and the other disclosed embodiments. A shield (not shown) can be interposed between the coil and the balloon to prevent cement from sticking to the balloon. Alternatively, a non-stick coating can be applied to the balloon.

Figure 22:
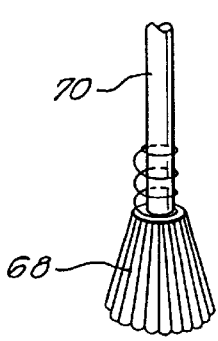
FIG. 22 depicts a cement restrictor and a tool.
Figure 23:
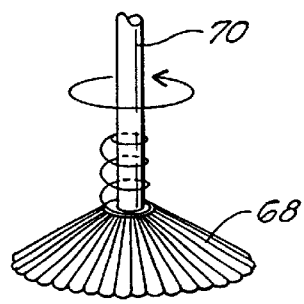
FIG. 23 depicts the tool of FIG. 22 being used to transition the cement restrictor from a first stable state to a second stable state.

Another way to apply stress to a stress responsive or merely deformable cement restrictor is shown in FIG. 22 which depicts a cement restrictor 68 engaged with a tool 70. The tool can be pressed or screwed through the cement restrictor to cause it to expand as shown in FIG. 23.

FIG. 30 illustrates yet another embodiment of a cement restrictor that includes one or more wires 72 embedded in a biocompatible material 74 such as polyethylene. The wire(s) 72 which can include memory material or ordinary copper, steel or the like, can be oriented longitudinally as shown. Following a temperature or stress change (removal or application) at least a portion of the cement restrictor expands.

Figure 32:
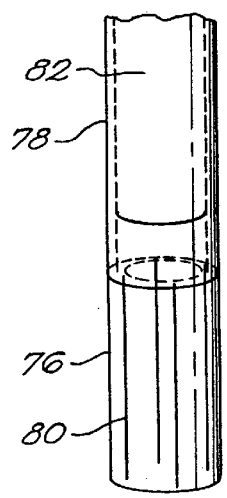
FIG. 32 illustrates yet another embodiment of a cement restrictor in association with a tool.
Figure 33:
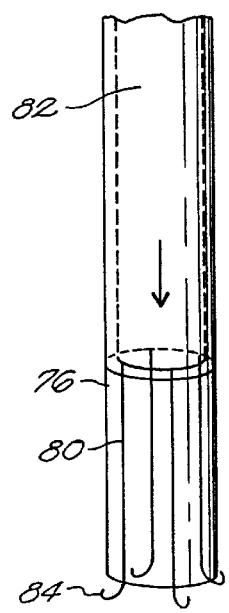
FIG. 33 illustrates shape memory structures being extended from an end of the cement restrictor of FIG. 32.
Figure 34:
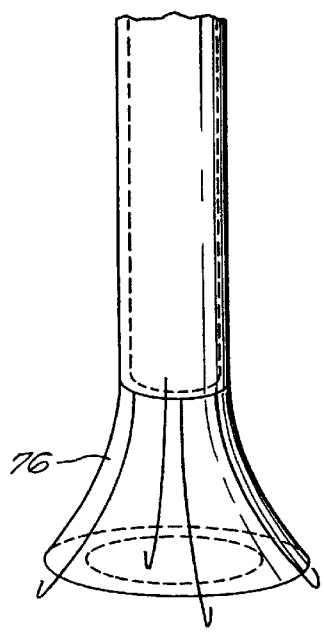
FIG. 34 illustrates the shape memory structures expanding the cement restrictor.
Figure 35:
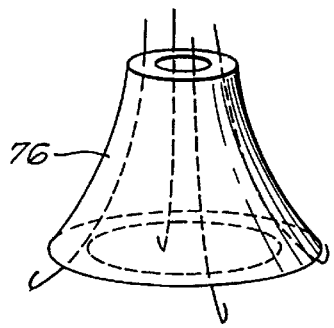
FIG. 35 illustrates the cement restrictor in an expanded state and disengaged from the tool.

FIGS. 32–35 illustrate yet another embodiment of a cement restrictor 76 in association with a tool 78. As shown in FIG. 32, the cement restrictor 76 includes channels through which one or more wires 80 are slidably disposed. The tool 78 includes a slidable portion 82 that can be moved toward the cement restrictor 76 to cause the wires to slide within the channels and extend from a free end of the cement restrictor as shown in FIG. 33. The portion of the wires free of the channels can be shaped as hooks or barbs 84 for bone engagement. The barbs also prevent the wire ends from retracting back into the channels. Following a temperature change, the cement restrictor 76 assumes an expanded configuration as shown in FIG. 34. Subsequently, the tool 78 is separated (such as by twisting) from the cement restrictor 76 as shown in FIG. 35.

Figure 36:
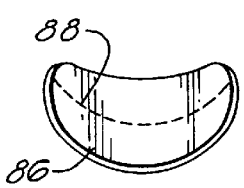
FIG. 36 illustrates a bistable structure in a first state.
Figure 37:
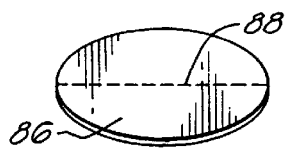
FIG. 37 illustrates a bistable structure in a second state.
Figure 38:
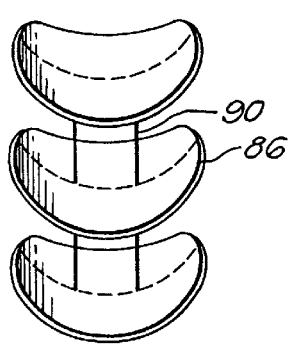
FIG. 38 depicts several bistable structures joined together in a reduced diameter configuration.

Turning now to FIG. 36, a bistable structure 86 is shown in a first state. FIG. 37 illustrates the bistable structure 86 in a second state. A deformable wire 88 is embedded within a biocompatible material to provide stable first and second states. In addition to the heat and stress applications described above, if the wire 88 is a memory material, an electric current can be used to cause a configuration transition. In one embodiment, a 250 miliamp current is adequate to activate the wire 88. Although a single bistable structure 86 can act as a cement restrictor, two or more bistable structures can be joined by a link 90, as shown in FIG. 38, to define a cement restrictor.

Figure 39:
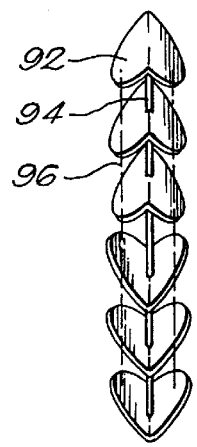
FIG. 39 depicts a bistable structure in a reduced diameter configuration.
Figure 40:
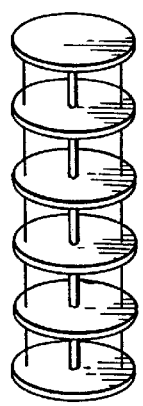
FIG. 40 illustrates the device of FIG. 39 in an increased diameter configuration.

FIG. 39 illustrates yet another embodiment of a cement restrictor that includes two or more flexible, biocompatible elements 92 joined to each other by one or more links 94. One or more wires 96 made of memory material are engaged with each of the elements 92. As shown in FIG. 39, the wires 96 are curved inward toward the longitudinal axis of the cement restrictor in a first state which causes outer portions of the elements 92 engaged with the wires to be drawn inward as well. As shown in FIG. 40, when the wires 96 are straight in a second state, they no longer bow inward. As the wires straighten, the elements 92 are pulled outward with the wire, causing the cement restrictor to have an increased diameter in the second state.

Figure 41:
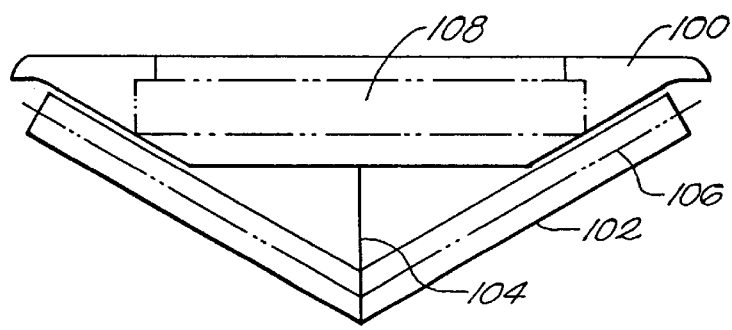
FIG. 41 illustrates still another embodiment of a cement restrictor in a reduced diameter configuration.

In addition to configurations that include both stress and temperature responsive shape memory components in a single structure described above, FIGS. 41–43 depict a cement restrictor that includes temperature responsive components that have different response or transition temperatures in a single device. Specifically, FIG. 41 depicts a cement restrictor having a first portion 100 joined to a second portion 102 by a linking element 104, wherein the first portion has fixed dimensions, and the second portion and the linking element have variable dimensions. Although a single second element and linking element are shown, additional elements that are substantially identical to the second element can be added to the structure with linking elements.

Figure 43:
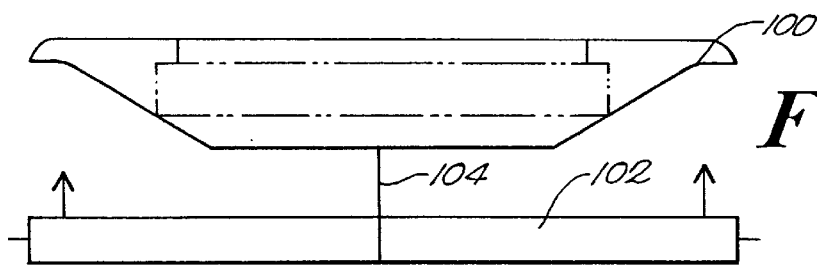
FIG. 43 illustrates the embodiment of FIG. 41 in a second stage of an increased diameter configuration.

In the exemplary embodiment, the first portion 100 includes a standard biocompatible metal such as Cobalt Chromium, the second portion includes UHMWPE having a Nitinol wire 106 embedded therein, and the linking element 104 is a Nitinol wire. It should also be noted that in this embodiment, as well in as the above described embodiments, a "wire" is understood to encompass a variety of cross-sectional geometries ranging from flat to square to circular or irregular. The wire 106 within the second element 102 has a transition temperature of 98.5° F. while the linking element 104 has a higher transition temperature of about 110° F. The difference in transition temperatures allows the cement restrictor to be reconfigured from a reduced diameter configuration as shown in FIG. 41 to an increased diameter configuration as shown in FIG. 43. A maximum transition temperature of 120° F. avoids tissue damage in the patient. As shown, the wire can extend beyond the edges of the second portion to improve bone engagement.

Figure 42:
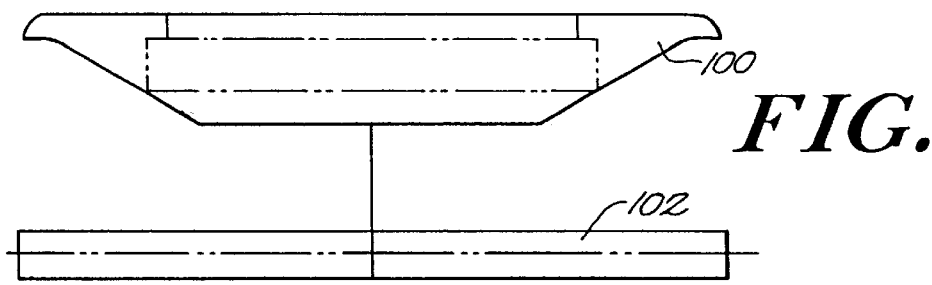
FIG. 42 illustrates the embodiment of FIG. 41 in a first stage of an increased diameter configuration.

In use, the cement restrictor is reconfigured as follows. The first portion 100 is positioned beyond the isthmus with the aid of a tool (not shown) that is engagable within an optional recess 108 in the first portion. Patient body heat causes the Nitinol in the second portion 102 to straighten, thereby increasing the diameter of the second portion as shown in FIG. 42. The UHMWPE composition chosen is resilient enough to be influenced to change shape and straighten with the embedded Nitinol wire(s), but still has enough rigidity to withstand cement pressurization. A heat gun (not shown) with a long nozzle that blows hot air (greater than 99° F. and less than 120° F.) is placed in the canal of the bone close to the first portion. This heat causes the activation of the linking element to decrease its length and to force the horizontal, now straightened, second portion closer to the first portion and also further into the narrower section of the isthmus. An alternative method to using a heat gun is to heat the wire with about one quarter ampere, since the resistance of the wire is proportional to the diameter of the wire (i.e. for a 0.006 inch diameter wire, 1 ohm/inch can be utilized). High frequency electromagnetic waves or ultrasound can also be used to activate the wire(s).

Although the invention has been shown and described with respect to exemplary embodiments thereof, various other changes, omissions and additions in form and detail thereof may be made without departing from the spirit and scope of the invention.

What is claimed is:

1. A cement restrictor comprising:
    a fluid impermeable configurable structure having at least one elongate deformable member disposed therein, the at least one deformable member being made of a shape memory material.
2. The cement restrictor of claim 1, wherein the structure is made of a biocompatible material.
3. The cement restrictor of claim 2, wherein the biocompatible material is polyethylene.
4. The cement restrictor of claim 2, wherein the elongate deformable member is a wire.
5. The cement restrictor of claim 4, wherein the wire is helical.
6. The cement restrictor of claim 1, wherein the configurable structure includes a cylindrical biocompatible body.
7. The cement restrictor of claim 1, wherein the configurable structure is bistable.
8. The cement restrictor of claim 7, wherein the configurable structure can be transitioned between a first stable state and a second stable state by application of an electric current.
9. The cement restrictor of claim 1, wherein the configurable structure is substantially conical and has a length along a longitudinal axis and a diameter extending radially from the longitudinal axis.
10. The cement restrictor of claim 9, wherein, the configurable structure includes at least one channel in which the elongate deformable member is slidably disposed.
11. The cement restrictor of claim 10, wherein at least a portion of the elongate deformable member extends from a portion of the conical structure.
12. The cement restrictor of claim 11, wherein the elongate deformable member includes a barbed periphery.
13. The cement restrictor of claim 1, wherein the configurable structure has a first end along a longitudinal axis and a second end opposite the first end, and wherein heating the configurable structure causes the second end to have a greater diameter than the first end.
14. The cement restrictor of claim 1, wherein the configurable structure has a first end along a longitudinal axis and a second end opposite the first end, and wherein cooling the configurable structure causes the second end to have a greater diameter than the first end.
15. The cement restrictor of claim 1, wherein the configurable structure has a first end along a longitudinal axis and a second end opposite the first end, and wherein stressing the configurable structure causes the second end to have a greater diameter than the first end.
16. A cement restrictor comprising:
    a fluid impermeable configurable structure having a substantially conical shape and a length along a longitudinal axis and a diameter extending radially from the longitudinal axis, and wherein the fluid impermeable configurable structure has a plurality of elongate deformable members disposed therein, and it includes a plurality of channels within which one of the plurality elongate members is slidably disposed.
17. The cement restrictor of claim 16, wherein at least a portion of each of the elongate deformable members extends from a portion of the conical structure.
18. The cement restrictor of claim 17, wherein each of the elongate deformable members includes a barbed periphery.

* * * * *